US010307229B2

(12) United States Patent
Hauth et al.

(10) Patent No.: US 10,307,229 B2
(45) Date of Patent: Jun. 4, 2019

(54) METHOD FOR CONSTRUCTING TOOTH SURFACES OF A DENTAL PROSTHESIS AND FOR PRODUCING DENTAL RESTORATIONS

(71) Applicant: DENTSPLY SIRONA Inc.

(72) Inventors: Steffen Hauth, Mainz (DE); Sascha Schneider, Mühltal (DE)

(73) Assignee: DENTSPLY SIRONA Inc., York, PA (US)

( * ) Notice: Subject to any disclaimer, the term of this patent is extended or adjusted under 35 U.S.C. 154(b) by 949 days.

(21) Appl. No.: 14/770,597

(22) PCT Filed: Mar. 3, 2014

(86) PCT No.: PCT/EP2014/054033
§ 371 (c)(1),
(2) Date: Aug. 26, 2015

(87) PCT Pub. No.: WO2014/131908
PCT Pub. Date: Sep. 4, 2014

(65) Prior Publication Data
US 2016/0000540 A1  Jan. 7, 2016

(30) Foreign Application Priority Data

Mar. 1, 2013 (DE) ........................ 10 2013 203 588

(51) Int. Cl.
G06F 17/50 (2006.01)
A61C 13/00 (2006.01)
G16H 20/40 (2018.01)
(52) U.S. Cl.
CPC ...... A61C 13/0004 (2013.01); A61C 13/0003 (2013.01); G16H 20/40 (2018.01)
(58) Field of Classification Search
CPC ................................................ A61C 13/0004
(Continued)

(56) References Cited

U.S. PATENT DOCUMENTS 7,796,811 B2  9/2010 Orth et al.
8,111,909 B2  2/2012 Orth et al.
(Continued)

FOREIGN PATENT DOCUMENTS

DE  10 2005 011 066 A1  9/2006
DE  10 2011 008 074 A1  7/2012
(Continued)

OTHER PUBLICATIONS

Jun. 20, 2014 International Search Report in PCT Application No. PCT/EP2014/054033, 4 pp.
(Continued)

*Primary Examiner* — Hugh M Jones
(74) *Attorney, Agent, or Firm* — Dentsply Sirona Inc.

(57) ABSTRACT

The invention relates to a method for constructing tooth surfaces of a dental prosthesis and for producing dental restorations, starting from a 3D data record of an upper mandible layout and a 3D data record of a lower mandible layout, each layout comprising a number of teeth arranged in each mandibular arch and the teeth of the upper mandible layout and the teeth of the lower mandible layout at intercuspation making contact with each other at multiple contact points. The contact surfaces are selected by approximation. Relevant surface pairs lying opposite one another are identified and are incorporated by an optimization algorithm into local minimum distances, taking into consideration surfaces that can slide past one another. This allows the desired contact points to be produced. Surfaces that have not been selected are not considered in the production of the points of contact.

12 Claims, 4 Drawing Sheets

(58) Field of Classification Search
USPC .......................................................... 703/6, 1
See application file for complete search history.

(56) References Cited

U.S. PATENT DOCUMENTS

| | | |
|---|---|---|
| 2004/0172150 A1 | 9/2004 | Perot et al. |
| 2006/0204078 A1 | 9/2006 | Orth et al. |
| 2011/0013827 A1 | 1/2011 | Orth et al. |
| 2012/0003604 A1 | 1/2012 | Moriyama et al. |
| 2012/0106833 A1 | 5/2012 | Orth et al. |
| 2013/0073265 A1 | 3/2013 | Kraemer et al. |
| 2013/0282351 A1 | 10/2013 | Tank |

FOREIGN PATENT DOCUMENTS

| | | |
|---|---|---|
| DE | 10 2011 005 899 A1 | 9/2012 |
| EP | 1 700 576 A1 | 9/2006 |
| EP | 2 389 892 A1 | 11/2011 |
| WO | 02/102270 A1 | 12/2002 |

OTHER PUBLICATIONS

Sep. 20, 2013 German Official Action in German Patent Appln. No. 10 2013 203 588.8, 8 pp.

METHOD FOR CONSTRUCTING TOOTH SURFACES OF A DENTAL PROSTHESIS AND FOR PRODUCING DENTAL RESTORATIONS

TECHNICAL FIELD

The present invention relates to a method for construction of tooth surfaces of a dental prosthesis and for production of dental restorations, starting from a 3D data record of a maxilla layout and a 3D data record of a mandible layout, each having multiple teeth positioned in the respective maxillary arch, wherein the teeth of the maxilla layout and the teeth of the mandible layout make contact with each other at multiple contact points in intercuspation.

In addition, the invention relates to a computer program as well as a data medium and use of a computer [for] control of the computer program.

However, adequate allocation of the maxillary layouts to one another is necessary to construct and produce tooth surfaces of dental prosthesis parts or to correct tooth positions.

PRIOR ART

Previous tools that are known and differ in convenience or precision pull the opposing jaws strictly until they come in rigid contact, without taking the morphology into account, or must be controlled completely manually.

In buccal registration and in a bite registration, also known as a squeeze bite, an alignment of the two jaws to one another is calculated by using one or more buccal pictures or bite registrations.

However, there are numeric limits to this method of setting a relationship.

The local resolution accuracy at the location of the picture necessarily determines, via the lever effect, the achievable accuracy of the fit on the opposing location at a distance.

For example, if a local accuracy of 25 µm is assumed, an effect of 200 µm is achieved on the opposite side of the jaw, which is, on the average, 8 cm away.

Doubling the scanning accuracy to 12 µm still creates an effect of 100 µm on the opposite side.

One possible optimization is the use of multiple locations for buccal registration or for the bite registration to ascertain the error.

This method can only be used when buccal registrations or squeeze bite information is available.

Another option for solving the problem is to allow, directly or after pre-registration, free mobility of the jaws relative to one another, translating in 3 axes in space, i.e., longitudinally displaceably, and rotationally about 3 axes in space.

The user must establish the contact situation freely by hand, purely visually, suspended in virtual 3D space, without thereby being able to rely on a feeling of physical contact, which he had on a true model.

It is known from DE 10 2005 011 066 A1 to define three desired points manually on a first and a second 3D data record of a model, wherein the points are contained in the first 3D data record as well as in the second, and to establish the correlation of the 3D data records.

Although a tooth surface of an opposing jaw may be included in a model, no different models are correlated.

It is a disadvantage that the desired maximal intercuspation cannot be taken into account in any of the cases known so far, as would happen in normal laboratory operation with plaster models clamped in an articulator.

Therefore, the determination of the desired contact points lags behind manual fitting and/or meets the methodological goals inadequately.

The object of the present invention is to provide a tool with which a user can create a desired contact situation for a given mandible and maxilla layout and thus determine the allocation to one another, in order to construct and produce tooth surfaces of dental prostheses parts or to correct tooth positions.

DESCRIPTION OF THE INVENTION

This object is achieved by the method according to the invention for construction of tooth surfaces of a dental prosthesis part and for production of dental restorations.

Starting from a 3D data record of a maxilla layout and a 3D data record of a mandible layout, each having several teeth arranged in the respective arch of the jaw, wherein the teeth of the maxilla layout and the teeth of the mandible layout have a multi-point contact having many contact points, the allocation is carried out with contact optimization, in that a common occlusal direction is automatically determined from the 3D data record of the maxilla layout and from the 3D data record of the mandible layout, the position of the teeth in the arch of the jaw is determined automatically in the 3D data record of the maxilla layout and in the 3D data record of the mandible layout, surface elements that are at least approximately opposite one another are identified automatically on at least one side on the basis of the position of the teeth in the arch of the jaw, as expected, and on at least one side of the opposing surface elements, the surface elements that are to come in contact are selected by the user and/or approximately automatically;

on the other side of the opposing surface elements, the surface elements that should come in contact are selected by the user and/or are selected approximately automatically;

regions that are present on both sides of the opposing surface elements are cut out and form surface pairs, only the cut-out surface pairs are minimized in their distance from one another by means of an optimization algorithm, such that the optimized allocation of the surface pairs can be transferred to the entire 3D data record of the maxilla layout and to the entire 3D data record of the mandible layout, and the construction of tooth surfaces of a dental prosthesis part as well as for production of dental restorations is done by using 3D data records allocated in this way.

Advantageously only surface pairs that can slide past one another can be taken into account.

Falsification of surface pairs on which there cannot be any contact are prevented by this choice.

The optimization algorithm can advantageously provide a non-penetrating overall layout of a 3D data record of a maxilla layout and a 3D data record of a mandible layout.

In optimization, it is possible to understand the working and the allocation of a real model due to this restriction.

An approximate allocation of the 3D data record of the maxilla layout and the 3D data record of the mandible layout can be achieved advantageously by pre-registration.

Pre-registration helps in defining the at least approximately opposing surface elements.

The selected surface elements can advantageously be projected automatically onto the respective other side in the occlusal direction and thus selected.

Thus an automatic transfer from regions selected on only one side to the other side is possible.

Only the surface elements for which there is a further need for optimization can advantageously be selected in a targeted manner.

The invention is thus based on a method in which the contact surfaces are marked approximately.

Unmarked surfaces are not taken into account for creating the contact.

On the whole, however, a non-penetrating overall layout is taken into account, such as that which also occurs with true plaster models in the articulator.

Relevant and opposing surface pairs are identified and are drawn into local distance minimums by optimization algorithm, taking into account surfaces that can slide past one another, which yields the desired contact points.

There may be a pre-registration of the jaws to simplify the allocation of the surfaces facing one another, which can be implemented in a user-friendly process with buccal registration, for example.

The invention also relates to a computer program, in particular a CAD/CAM program that can be controlled by the method according to the invention.

The computer program is set up to display on a monitor at least one 3D data record of a maxilla layout or one 3D data record of a mandible layout, wherein the 3D data record has a mark indicating a state of the computer program into which the computer program can be brought by allocation of the 3D data records.

The invention further relates to a data medium which stores the computer program according to the invention.

It also relates to a computer for controlling a computer program.

BRIEF DESCRIPTION OF THE DRAWINGS

Exemplary embodiments of the present invention are illustrated in the drawings and explained in greater detail in the following description.

In the figures.

EXAMPLE

In one embodiment of the present invention, a CAD/CAM program is carried out on a device for construction of tooth surfaces of a dental prosthesis part and producing dental restorations (for example, CEREC, AC+MC, XL from the present applicant).

Figure 1:
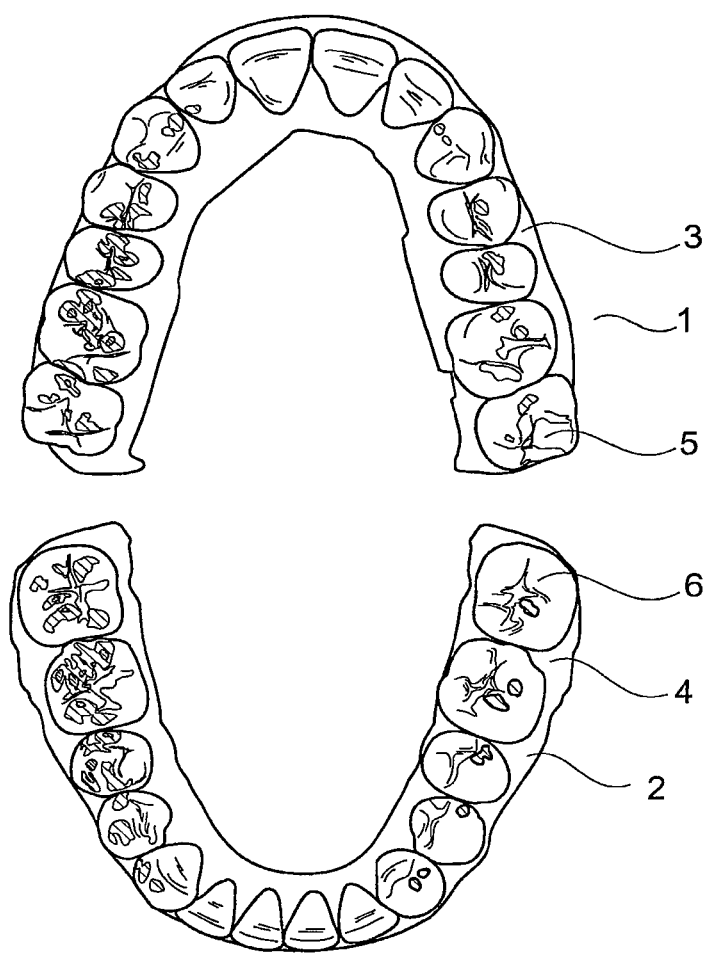
FIG. 1 shows a 3D data record of a maxilla layout and a 3D data record of the respective mandible layout in an approximate alignment with one another.

The CAD/CAM program is set up to display on a screen a 3D data record 1, shown in FIG. 1, of a maxilla layout and a 3D data record 2 of a mandible layout, each having multiple teeth 5, 6 arranged in the respective arch of the jaw 3, 4.

A common occlusal direction is determined automatically in the known way from the 3D data record 1 of the maxilla layout and the 3D data record 2 of the mandible layout.

In addition, the position of the teeth 5, 6 in the arch of the jaw 3, 4 is determined automatically in a known way in the 3D data record 1 of the maxilla layout and in the 3D data record 2 of the mandible layout.

Since the teeth 5 of the maxilla layout 1 and the teeth 6 of the mandible layout 2 have a multi-point contact with many contact points at intercuspation, which is unknown given separate detection of the 3D data records, an allocation must first be established by correlation of the 3D data records.

The procedure for this is as follows: on the basis of the positions of the teeth 5, 6 in the arch of the jaw 3, 4, at least approximately opposite surface elements on at least one side, i.e., on one of the two jaw layouts, are identified automatically, as expected.

Figures 2, 4A, 4C:
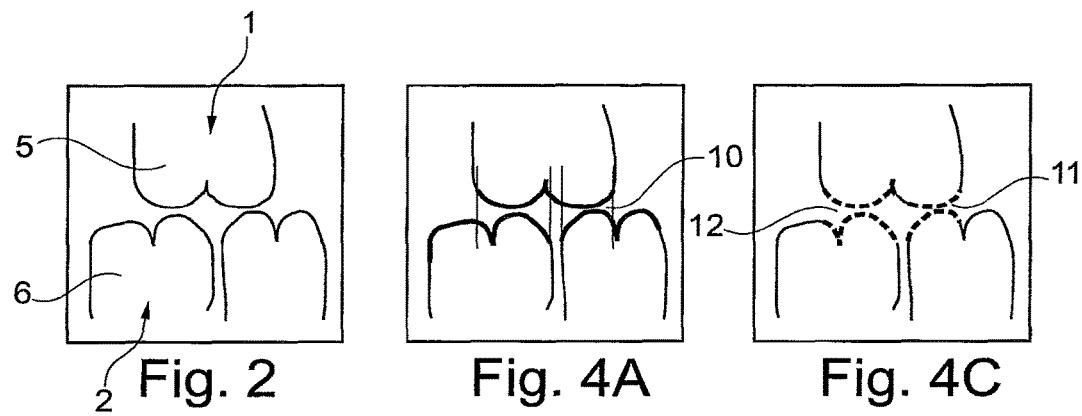
FIG. 2 shows a section through the two 3D data records approximately aligned with one another as a basic diagram with opposing surface elements identified.
FIG. 4A shows regions delimited by projection in the occlusion direction.
FIG. 4c shows the cutout regions from FIG. 4B used for the optimization.

FIG. 2 shows a section through the two 3D data records 1, 2, which are approximately aligned with one another, as a basic diagram with opposing surface elements identified on teeth 5, 6.

Figures 3, 4B:
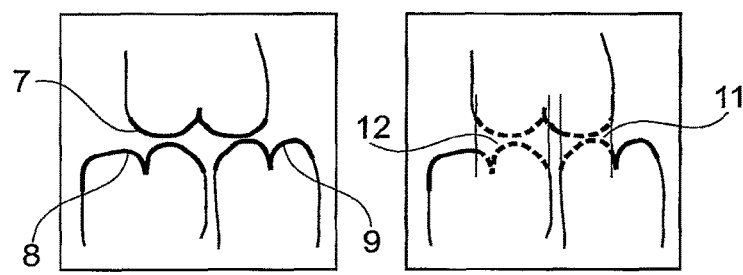
FIG. 3 shows the selected surface elements on both sides considered for an allocation.
FIG. 4B shows the delimited regions from FIG. 4A as opposing marked surface pairs.

FIG. 3 shows the selected surface elements 7-9 in question for an allocation on both sides, i.e., in the 3D data record 1 of the maxilla layout and in the 3D data record 2 of the mandible layout.

The surfaces which should come in contact are selected automatically or approximately by the user.

On the other side of the opposing surface elements, the surface elements that should come in contact are selected by the user and/or approximately automatically.

The surfaces can be determined in various ways: by user input, automatically with the help of the geometry of the tooth, in particular the curvature, automatically with the help of bioenergetics, automatically on the basis of a height parameter, and certain surface portions can be included and certain surface portions can be excluded.

This choice can be made by the user, for example, by painting the 3D model, clicking [and] drawing bordering lines, and can be transferred automatically to the opposite jaw by pre-registration of the jaws relative to one another.

There may be a trend toward "too many" surfaces, i.e., even those marked with good contact already or, in a targeted manner, only those for which there is a further need for optimization.

FIG. 4A shows regions of allocated surface elements, which, after the choice according to FIG. 3, can be delimited by an automatic projection onto the respective other side in the occlusive direction, represented by the straight lines 10.

FIG. 4B shows the regions from FIG. 4A, delimited by the projection, as selected opposing surface pairs 11, 12, and FIG. 4c shows the cut-out regions from FIG. 4B, which are used for the optimization and which are present on both sides of the opposing surface elements and form surface pairs 11, 12.

The contact is optimized by the fact that only the cut-out surface pairs are minimized in their distance from one another by means of an optimization algorithm, e.g., a downhill-simplex method with a suitable evaluation function of the surfaces.

The contact layout is improved by the fact that only these non-contiguous regions are used instead of the model of the entire jaw.

The optimized allocation of the surface pairs is transferred to the entire 3D data record of the maxilla layout and to the entire 3D data record of the mandible layout.

FIGS. 5-8 show a screenshot of the surfaces drawn and the before/after situation compared with the actual genuine contact situation on the plaster model in the articulator.

It can be seen that it is even possible to resolve existing penetrations of a pre-registration as well as to create the desired genuine contacts.

Furthermore, in comparison with the model in the articulator with genuine contacts colored by means of contact film, this shows how realistic and accurate the calculated result is.

Figure 5:
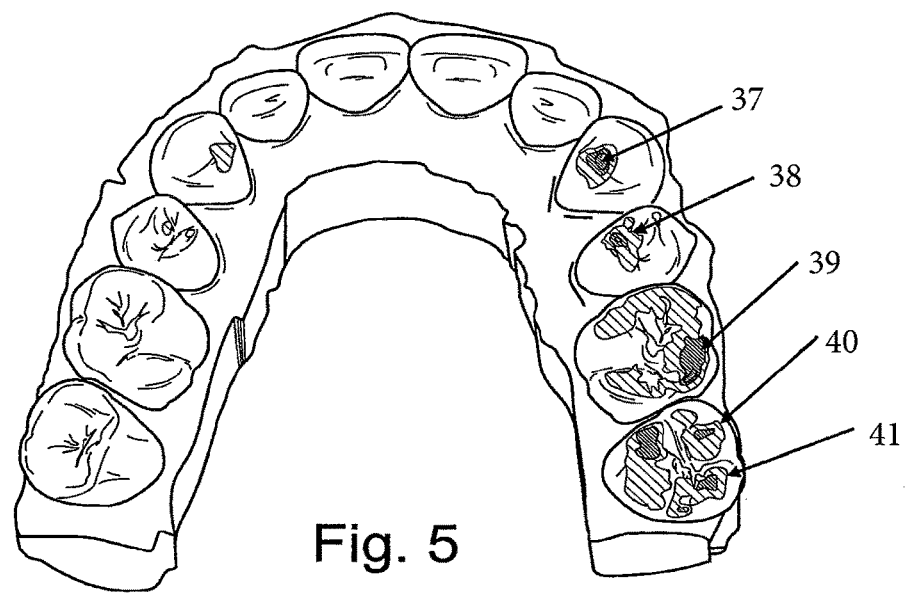
FIG. 5 shows a 3D data record of the maxilla after pre-registration with an initial contact situation.

FIG. 5 shows a 3D data record of the maxilla after pre-registration with an initial contact layout.

In the example, the one jaw half has too little contact and the other jaw half tends to have too much contact, as indicated by the arrows 37-41 and even penetrations.

Figure 6:
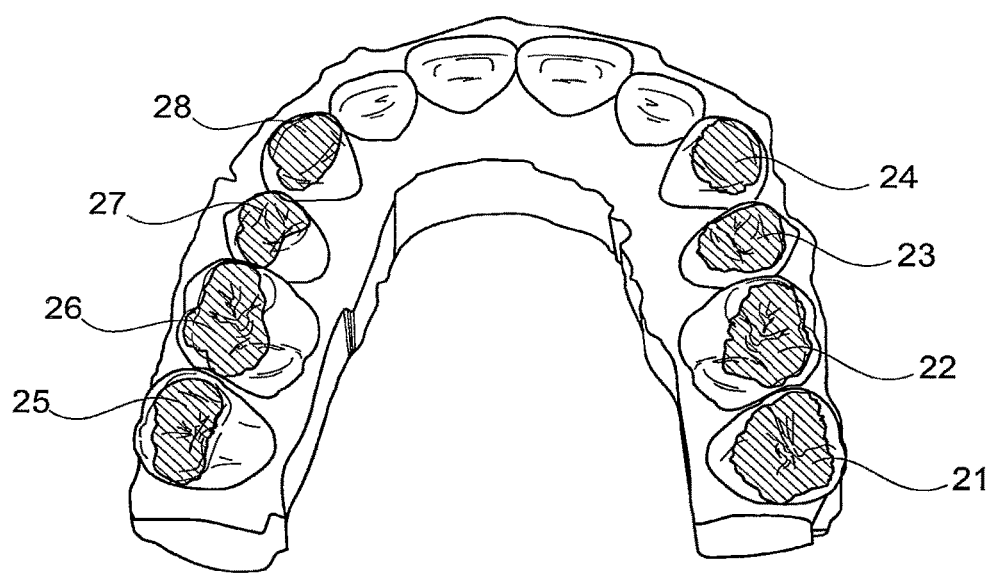
FIG. 6 shows the 3D data record from FIG. 5 with selected surface elements.

To carry out the method according to the invention, surface elements 21-28 on the teeth are selected as shown in FIG. 6 in the 3D data record from FIG. 5, on both sides of the jaw in the example, because there is a need for optimization of the pre-registration on both sides.

Figure 7:
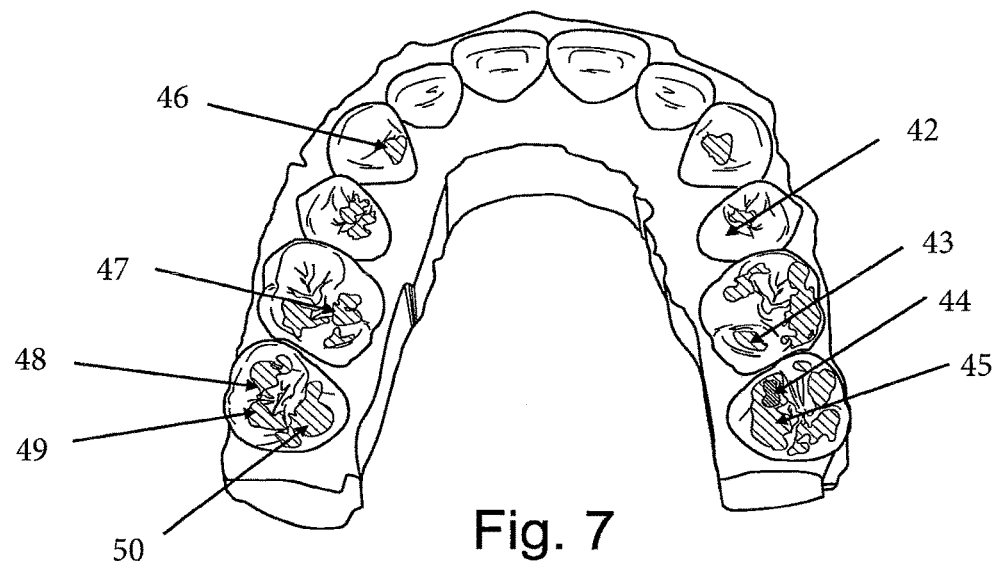
FIG. 7 shows the 3D data record of the maxilla from FIG. 5 with a contact situation after optimization.

FIG. 7 shows the 3D data record of the maxilla from FIG. 5 with a contact situation after optimization, where the contact points are again indicated by arrows 42-50.

Figure 8:
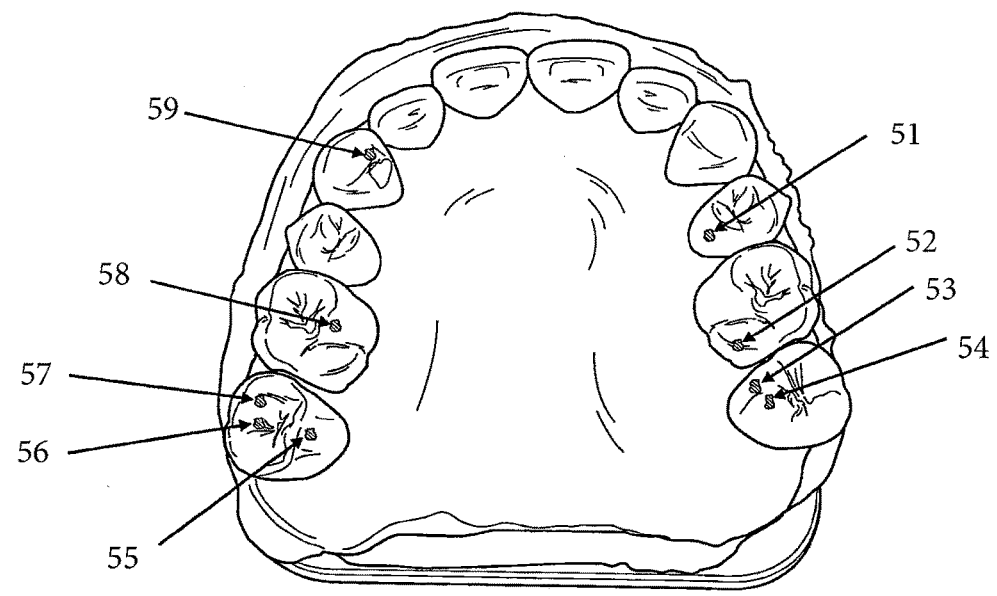
FIG. 8 shows a comparison of the maxilla as a plaster model with a contact situation in the articulator with maximal intercuspation.

A comparison with the contact situation of a maxilla, shown in FIG. 8, as a plaster model in the articulator at maximal intercuspation, shows a correspondence at all the essential contact points, which are indicated here again by arrows 51-59.

On the basis of a model allocated in this way, the construction of tooth surfaces of a dental prosthesis part and for production of dental restorations can be carried out using 3D data records allocated in this way.

A sequential procedure is conceivable, e.g., for creating a vertical increase in occlusion, so that, e.g., even after successfully creating a restoration, this method can be applied again to a model scan, including restorations then calculated.

Figure 9:
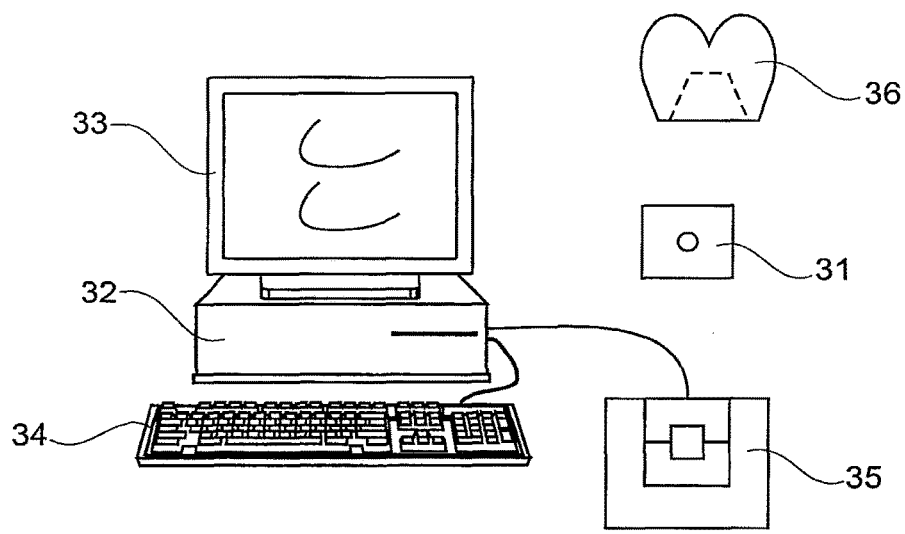
FIG. 9 shows a data medium, a computer for carrying out the method and a processing machine for producing the dental prosthesis part.

FIG. 9 shows a data medium 31 on which the computer program is stored, a computer 32 having a monitor 33 and input means 34 for carrying out the method, and a processing machine 35 for producing a dental prosthesis part 36, which is illustrated as a crown in a great magnification.

The invention claimed is:

1. A method for the construction of tooth surfaces of a dental prosthesis part and for producing dental restorations, comprising:
   allocating a 3D data record of a maxilla layout and a 3D data record of a mandible layout to each other by performing contact optimization, with each layout having a plurality of teeth arranged in the respective arch of the jaw, wherein the teeth of the 3D data record of the maxilla layout and the teeth of the 3D data record of the mandible layout have a multi-point contact with numerous contact points in intercuspation, the method further comprising:
   automatically determining a common occlusal direction from the 3D data record of the maxilla layout and from the 3D data record of the mandible layout,
   automatically determining the position of the teeth in the arch of the jaw in the 3D data record of the maxilla layout and in the 3D data record of the mandible layout,
   automatically identifying surface elements that are at least approximately opposite one another on at least one side of the opposing surface elements on the basis of the position of the teeth in the arch of the jaw, and
   (a) selecting, by a user and/or (b) selecting automatically or substantially automatically, on one side of the opposing surface elements, the surface elements that are to come in contact;
   (a) selecting, by a user and/or (b) selecting automatically or substantially automatically, on the other side of the opposing surface elements, the surface elements that are to come in contact;
   cutting out regions that are present on both sides of the opposing surface elements to form surface pairs,
   minimizing the cut-out surface pairs in their distance from one another using an optimization algorithm, such that the optimized allocation of the surface pairs is transferred to the 3D data record of the maxilla layout and to the 3D data record of the mandible layout, and
   fabricating one or more dental restorations based on the 3D data record of the maxilla layout and the 3D data record of the mandible layout.

2. The method according to claim 1, wherein only surface pairs that can slide past one another are used.

3. The method according to claim 1, wherein the optimization algorithm supplies a non-penetrating overall layout of the 3D data record of a maxilla layout and of the 3D data record of a mandible layout.

4. The method according to claim 1, wherein an approximate allocation of the 3D data record of the maxilla layout and of the 3D data record of the mandible layout is obtained via pre-registration.

5. The method according to claim 4 wherein the pre-registration is a buccal registration.

6. The method according to claim 1, wherein the selected surface elements in the occlusal direction are projected automatically onto the respective other side, and the regions that are present on both sides of the opposing surface elements are cut out and form said surface pairs.

7. The method according to claim 1, wherein only the surface elements for which there is a need for further optimization are selected in a targeted manner.

8. The method according to claim 1, wherein the optimization algorithm is a downhill-simplex method.

9. The method according to claim 1, wherein the surface elements are selected based on one or more members of the group consisting of user input, geometry of teeth, bioenergetics and a height parameter.

10. A non-transitory computer-readable storage medium storing a program which, when executed by a computer system, causes the computer system to perform the method of claim 1.

11. A system for the construction of tooth surfaces of a dental prosthesis part and for producing dental restorations, the system comprising:
   a processing machine for producing the dental prosthesis part, and
   at least one processor configured to perform the steps of:

allocating a 3D data record of a maxilla layout and a 3D data record of a mandible layout to each other by performing contact optimization, with each layout having a plurality of teeth arranged in the respective arch of the jaw, wherein the teeth of the 3D data record of the maxilla layout and the teeth of the 3D data record of the mandible layout have a multi-point contact with numerous contact points in intercuspation, automatically determining a common occlusal direction from the 3D data record of the maxilla layout and from the 3D data record of the mandible layout, automatically determining the position of the teeth in the arch of the jaw in the 3D data record of the maxilla layout and in the 3D data record of the mandible layout, automatically identifying surface elements that are at least approximately opposite one another on at least one side of the opposing surface elements on the basis of the position of the teeth in the arch of the jaw, and (a) enabling selecting, by a user and/or (b) selecting automatically or substantially automatically, on one side of the opposing surface elements, the surface elements that are to come in contact;

(a) enabling selecting, by a user and/or (b) selecting automatically or substantially automatically, on the other side of the opposing surface elements, the surface elements that are to come in contact;

cutting out regions that are present on both sides of the opposing surface elements to form surface pairs, minimizing the cut-out surface pairs in their distance from one another using an optimization algorithm, such that the optimized allocation of the surface pairs is transferred to the 3D data record of the maxilla layout and to the 3D data record of the mandible layout, and fabricating one or more dental restorations based on the 3D data record of the maxilla layout and the 3D data record of the mandible layout.

12. A method for the construction of tooth surfaces of a dental prosthesis part using a computer, wherein the computer comprising a processor and a software program having instructions stored in a non-transitory readable medium, when executed, causes computer to perform the method including steps of:

allocating a 3D data record of a maxilla layout and a 3D data record of a mandible layout to each other by performing contact optimization, with each layout having a plurality of teeth arranged in the respective arch of the jaw, wherein the teeth of the 3D data record of the maxilla layout and the teeth of the 3D data record of the mandible layout have a multi-point contact with numerous contact points in intercuspation, automatically determining a common occlusal direction from the 3D data record of the maxilla layout and from the 3D data record of the mandible layout, automatically determining the position of the teeth in the arch of the jaw in the 3D data record of the maxilla layout and in the 3D data record of the mandible layout, automatically identifying surface elements that are at least approximately opposite one another on at least one side of the opposing surface elements on the basis of the position of the teeth in the arch of the jaw, and (a) enabling selecting, by a user and/or (b) selecting automatically or substantially automatically, on one side of the opposing surface elements, the surface elements that are to come in contact;

(a) enabling selecting, by a user and/or (b) selecting automatically or substantially automatically, on the other side of the opposing surface elements, the surface elements that are to come in contact;

cutting out regions that are present on both sides of the opposing surface elements to form surface pairs, and minimizing the cut-out surface pairs in their distance from one another using an optimization algorithm, such that the optimized allocation of the surface pairs is transferred to the 3D data record of the maxilla layout and to the 3D data record of the mandible layout.

\* \* \* \* \*